US006506730B1

(12) United States Patent
Lee et al.

(10) Patent No.: US 6,506,730 B1
(45) Date of Patent: Jan. 14, 2003

(54) NASAL TRANSMUCOSAL DELIVERY OF PEPTIDE CONJUGATED WITH BIOCOMPATIBLE POLYMERS

(76) Inventors: Kang Choon Lee, 86-12 Nonhyeon-dong, Kangnam-ku, 135-010, Seoul (KR); Myung-Ok Park, #107-1403 Hakyeoul Chungnu Apt., Nowon-ku, 139-230, Seoul (KR)

( * ) Notice: Subject to any disclaimer, the term of this patent is extended or adjusted under 35 U.S.C. 154(b) by 0 days.

(21) Appl. No.: 09/639,483

(22) Filed: Aug. 15, 2000

(30) Foreign Application Priority Data

Aug. 17, 1999 (KR) .............................. 99-33984

(51) Int. Cl.[7] ..................... A61K 38/09; A61K 38/17; A61K 38/23; A61K 38/28; A61K 38/29
(52) U.S. Cl. ................... 514/12; 514/2; 514/3; 514/21; 530/302; 530/303; 530/307; 530/313; 530/345
(58) Field of Search .............. 514/2, 3, 8, 12, 514/15, 17, 21; 530/302, 303, 307, 313, 345

(56) References Cited

U.S. PATENT DOCUMENTS 5,681,811 A * 10/1997 Ekwuribe ................. 514/8
6,165,509 A * 12/2000 Hoffman et al. ........... 424/487

FOREIGN PATENT DOCUMENTS

WO          97/40070     * 10/1997

OTHER PUBLICATIONS

Lee et al. Preparation and characterization of Polyethylene . . . Pharm. Dev. Tech. vol. 4, No. 2, pp. 269–275, May 1999.*

Lee et al. Isolation, Characterization, and Stability of . . . Pharm. Res. vol. 16, No. 6, pp. 813–818, Jun. 1999.*

Morimoto, Kazuhiro, et al. *Effects of Proteolytic Enzyme Inhibitors on Nasal Absorption of Salmon Caciton in Rats*, International Journal of Parmaceutics, vol. 113 (1995) 1–8.

Dua, Ramneik, et al. *The Influence of Tonicity and Viscosity on the Intranasal Absorption of Salmon Calcitonin in Rabbits*, International Journal of Pharmaceutics, vol. 147 (1997) 233–242.

* cited by examiner

Primary Examiner—Jeffrey E. Russel
(74) Attorney, Agent, or Firm—Roberts & Mercanti, LLP (57) ABSTRACT

The present invention relates to a pharmaceutical composition for the nasal transmucosal delivery of a biocompatible polymer-biologically active peptide conjugate. The pharmaceutical composition of the present invention increases the water solubility of peptide, which is sparingly soluble in water, improves its stability by protecting it from being degraded by proteases. As a result, the number of administrations of the drug and the side-effects induced by drug abuse are decreased. In addition, since the pharmaceutical composition of the present invention is delivered through the nasal cavity, it allows drug activity to be expressed in a short period of time and improves a bioavailability.

8 Claims, 7 Drawing Sheets

SEQUENCE LISTING

<160> NUMBER OF SEQ ID NOS: 3

<210> SEQ ID NO 1
<211> LENGTH: 4
<212> TYPE: PRT
<213> ORGANISM: Human
<220> FEATURE:
<221> NAME/KEY: misc_feature
<222> LOCATION: (1)..(4)
<223> OTHER INFORMATION: First 4 residues of met or leu enkaphalin -continued

```
<400> SEQUENCE: 1

Tyr Gly Gly Phe
1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      GHRP-6

<400> SEQUENCE: 2

His Asp Tyr Ala Tyr Asp Lys
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      LH-RH

<400> SEQUENCE: 3

Glu His Trp Ser Tyr Gly Leu Arg Pro Gly
1               5                   10
```

NASAL TRANSMUCOSAL DELIVERY OF PEPTIDE CONJUGATED WITH BIOCOMPATIBLE POLYMERS

FIELD OF THE INVENTION

The present invention relates to a pharmaceutical composition for a nasal transmucosal delivery, comprising a biologically active peptide, which is sparingly soluble in water, conjugated with an active biocompatible polymer.

More particularly, the present invention relates to the pharmaceutical composition containing the biocompatible polymer-biologically active peptide conjugate suitable for use in the nasal transmucosal delivery, which is highly improved in water solubility and protected from being degraded by protease.

The pharmaceutical composition comprising of the peptide-polymer conjugate for the nasal transmucosal delivery of the present invention allows drug activity to be expressed in a short period of time and improves bioavailability.

BACKGROUND

In the body, various peptides play important roles, existing as various forms such as hormones and cytokines. With recent great advances in genetic engineering, various peptides have been able to be synthesized on a mass scale and be used as medicines.

Use of peptides or proteins as medicines, however, suffers from many problems. First, peptides or proteins are very low in body absorption efficiency because they are easily hydrolyzed or degraded by enzymes within a short period of time after being taken into the body. Further, when such peptide medicines are repetitively administered, immune reactions are frequently induced to produce antibodies which may cause so serious hypersensitivity as to menace the life of the administered, acting as a neutralizing role against the physiological activity of the medicines. In addition, the clearance attributable to the reticuloendothelial system (RES) is increased. Therefore, most of peptide medicines have been administered by injection, thus far.

Injection administration, however, gives patients pain and has accompanying dangers. Particularly, patients who need to be treated for a long period of time may not be able to treat themselves by injection. Thus, there remains a need to develop other routes for peptide administration.

An adult's nasal cavity is coated with a mucosa at a thickness of 2.0–4.0 mm (Mugind, Nasal Allergy, Blackwell Scientific, Oxford, 1979) and has a volume of about 20 ml. It is thought that the nasal cavity allows drug activity to be expressed in a short period of time because of its being abundant in fine villus and large in absorption surface area. Accordingly, extensive research has been made on the transmucosal delivery of drugs. Factors which have influence on the absorption of drugs through mucosae include physical and chemical properties of drugs, such as drug's inherent transmittance, ion strength, flow distribution coefficient and molecular weight, carrier transportation, protease degradation, and physiological conditions of nasal mucosae. In fact, the nasal mucosa is a direct absorption route through which drugs can circumvent the liver metabolism, which is a great hindrance to the utilization of drugs in the body upon oral administration. Thus, the nasal transmucosal route has an advantage over the oral route in that the body utilization of drugs can be significantly improved.

The nasal transmucosal delivery of peptides or proteins of large molecular weights are lower in absorption efficiency than intravenous injection because the peptides or proteins cannot pass well through nasal mucosae. Absorption promoters have been suggested to improve the absorption of peptides.

Examples of suggested absorption promoters include surfactants (Hirai et al., Int. J. Pharm. 9, 165–169, 1981), acylcarnitine, cholinester, alpha-cyclodextrin, and chelating agents (Lee, In: Delivery Systems for Peptide Drug, Plenum, New York, pp 87–104, 1986).

These absorption promoters, however, are difficult to apply in practice because they give rise to a decrease in the stability of the drugs upon formulation, or irritate nasal mucosae.

In regard to the nasal transmucosal delivery of drugs, many research results are disclosed in patents.

European Pat. Nos. 23,359 and 122,023 open the possibility that a powder formulation of peptide drugs is delivered through nasal mucosae. U.S. Pat. No. 4,250,163 discloses a mucosa-adsorptive substance which is admixed with a powder form of peptides drugs to enhance the nasal transmucosal delivery of the drugs. European Pat. No. 123,831 is directed to the administration of steroids through nasal mucosae.

German Pat. No. 2,620,446 describes a body absorption enhancer which is effective for the nasal transmucosal delivery of insulin.

PCT/GB/86/00721 discloses a formulation technique of drugs into microspheres which can be delivered through nasal mucosae. However, this formulation technique can be applied only to particular drugs.

In Japanese Pat. No. Sho. 58-189118, cyclodextrin is utilized for the nasal transmucosal delivery of peptides. Japanese Pat. No. Sho. 59-89619 discloses ethereal surfactants, for example, polyoxyethylene lauryl ether, as neutral absorption enhancers for nasal transmucosal delivery. However, these surfactants are not suitable for clinical use because they cause damage to nasal mucosae.

Japanese Pat. No. Sho. 61-118325 describes alkaline or neutral amino acids for use in the nasal transmucosal delivery of calcitonin. In Japanese Pat. No. Sho. 63-39822, sucrose fatty acid ester is used as an absorption promoter for the nasal transmucosal delivery of drugs. However, these absorption promoters are also toxic to mucosae.

The above-mentioned reference patents, most of which are based on the sustained release of peptide drugs, enable drugs to be released continuously, but cannot solve the problem that peptides or protein drugs administered through mucosae are degraded in a short period of time. These conventional techniques find difficulty in being applied for the nasal transmucosal delivery of peptide drugs.

Conjunction of pharmaceutically active proteins or molecules to synthetic macromolecules may afford great advantages when they are applied in vivo and in vitro. When being covalently bonded to macromolecules, physiologically active molecules may be changed in surface properties and solubility. For example, their solubility in water or organic solvents may be increased. Further, the presence of macromolecules may make the conjugated peptides more stable in vivo as well as reduce the clearance attributed to the intestinal system, the kidney, the spleen and/or the liver. Hence, conjunction of polymers to peptides can bring about a great improvement in the stability of the peptides in solutions and effectively protect the intrinsic surface properties of peptides to prevent non-specific protein adsorption.

U.S. Pat. No. 4,179,337 discloses conjugates between peptides or polypeptides and polyethylene glycol (hereinafter, referred to as "PEG") with a molecular weight of 500–20,000 or water-soluble polymers, which are reduced in antigenicity and anti-immunity while maintaining the biological activity of the peptides or polypeptides. It is described in U.S. Pat. No. 4,301,144 that hemoglobin is increased in oxygen molecule-carrying potential when being associated with PEG or water-soluble polymers.

Various proteins are reported to show extended half-life spans and reduced immunogenicity in plasma when being conjugated with PEG (Abuchowski et al., Cancer Biochem. Biophys., 7, 175–186, 1984). Uricase-PEG conjugates are demonstrated to be increased in in-vivo half life span and show reduced side-effects during the metabolism of uric acid (Davis et al., Lancet, 2, 281–283, 1981).

As apparent from the preceding patents, the conjugation of PEG allows biologically active peptides or proteins to be increased in-vivo half life span and solubility and to be reduced in immune reactions.

Most frequently, the conjugation of PEG to polypeptides is achieved by reacting activated PEG to amino residues of polypeptides. Suitable for use in this purpose are a lysine residue and N-termini. As for PEG activation, one of the hydroxy groups of PEG is substituted with a methyl ether group while the other hydroxy group is bonded to an electrophile functional group (Abuchowski, A. and Davis, F. F. (1981), in Enzymes as Drugs (Holsenberg, J. and Roberts, J., eds.)). Examples of activated polymers include PEG-N-hydroxysuccineimide-activated esters, which contain amide bonds, PEG-epoxides and PEG-tresylate, which contain alkyl bonds, PEG-carbonyl imidazole and PEG-nitrophenyl carbonates, which contain urethane bonds, PEG-aldehyde, which contains a Schiff's base at the N-terminus.

On a polypeptide sequence, lysine residues are randomly located, so that PEG is non-specifically bonded to the polypeptide. In order to obtain uniform PEG-peptide conjugates, there have been made attempts of bonding PEG to targeted sites such as cysteine residues, oligo sugars, hydroxy groups, arginine groups.

Examples of PEG derivatives able to specifically react to cysteine groups of polypeptides include PEG-vinyl sulphone, PEG-iodoacetamide, PEG-maleimide, and PEG-orthopyridyl disulfide with most preference to maleimide-containing PEG. PEG-vinyl sulfone is best in view of the stability in water solutions while PEG-orthopyridyl disulfide can be reversibly degraded in vivo because of the presence of disulfide bonds.

Peptides taking advantage of these derivatives can be exemplified by interleukin-3 and interleukin-2.

PEG derivatives reactive specifically to oligo sugars of polypeptides may be exemplified by PEG-hydrazide, which is able to react with aldehyde-containing compounds to form relatively stable hydrazone bonds. Advantage is taken of the specific bonding of PEG-hydrazides to sugar moieties of glycoproteins.

PEG-isocyanates react specifically with hydroxy groups of polypeptides. In order to conjugate PEG to arginine residues of polypeptides, there is used PEG derivatives containing phenylglyoxal, which is highly reactive to the guanidino group.

As mentioned above, the nasal transmucosal delivery of peptides alone is significantly improved in absorption efficiency compared with the oral administration because the peptides are not subjected to liver metabolism, but poor in the bioavailability of the peptides because they are degraded by endogenous enzymes.

To overcome the foregoing and other disadvantages, we, the inventors of the present invention, have developed a pharmaceutical composition for the nasal transmucosal delivery, comprising a sparingly soluble, biologically active polypeptide conjugated with an activated biocompatible polymer. The present invention have confirmed that, when the polymer-peptide conjugate is administered through the nasal cavity, it is improved in water solubility and protected from being degraded by proteases, whereby the medicinal activity of the pharmaceutical composition can be sustained for an extended period of time in vivo.

SUMMARY OF THE INVENTION

It is an object of the present invention to provide a biologically active peptide-polymer conjugate suitable for use in a nasal transmucosal delivery.

Further objects and advantages of the present invention will appear hereinafter.

The present invention provides a pharmaceutical composition for the nasal transmucosal delivery, comprising a sparingly soluble, biologically active polypeptide conjugated with an activated biocompatible polymer.

Further features of the present invention will appear hereinafter.

BRIEF DESCRIPTION OF THE DRAWINGS

●; mono-PEG-sCT(N-terminal conjugate, M1).

■; mono-PEG-sCT(Lys$^{18}$-conjugate, M2).

♦; mono-PEG-sCT(Lys$^{11}$-conjugate, M3).

▲; sCT,

□; mono-PEG-sCT not isolated its isomers.

DETAILED DESCRIPTION OF PREFERRED EMBODIMENTS

The term "biocompatible polymers" as used herein means naturally occurring or synthetic compounds which are dissolved in water. By way of example, not limitation, the biocompatible polymers include polyethylene glycol, polypropylene glycol (PPG), polyoxyethylene (POE), polytrimethylene glycol, polylactic acid and its derivatives, polyacrylic acid and their derivatives, polyamino acid, polyvinyl alcohols, polyurethane, polyphosphazene, poly(L-lysine), polyalkylene oxide (PAO), and water-soluble polymers such as polysaccharide, dextran, and non-immunogenic polymers such as polyvinyl alcohol and polyacryl amide.

Available in the present invention are polymers ranging in molecular weight of from about 200 to about 20,000 and preferably from about 500 to about 12,000.

The present invention provides a peptide-polymer conjugate for a nasal transmucosal delivery, which can be prepared by bonding an activated polymer to a biologically active peptide. In this regard, the bond between the peptides and the polymers may be a covalent bond or a non-covalent bond such as a lipophilic bond or a hydrophobic bond.

In preparing the peptide-polymer conjugates of the present invention, the molar ratio of polypeptides to activated polymers are in the range of from about 1:1 to about 1:10 and preferably in the range of from about 1:1 to about 1:7. In addition, one to three activated polymers may be conjugated to one polypeptide molecule. Peptide-mono polymer conjugates exert the most effective pharmaceutical activity. In the case of calcitonin-PEG conjugates, PEG can be conjugated to the N-terminus of calcitonin and/or Lys$^{18}$ and/or Lys$^{11}$. Of the resulting calcitonin-PEG conjugates, the calcitonin-(mono) PEG conjugate in which one PEG molecule is conjugated to one calcitonin molecule exhibits the highest calcium reduction effect. A conjugate isomer in which PEG is conjugated to the N-terminus or the Lys$^{18}$ shows more sustained and effective calcium reduction activity than does a conjugate isomer in which PEG is conjugated to Lys$^{11}$. At pH 5, 6 or 7 of the reaction solution, more than 80% of PEG is conjugated to the N-terminus of calcitonin. On the other hand, at pH 8 or higher, PEG is increasingly conjugated to Lys$^{11}$ and Lys$^{18}$. In contrast, changes in reaction time and molar ratio cannot affect the proportion of isomers.

The binding reaction of the peptide-activated polymer in the present invention is performed in 0.1 M phosphate buffer ranged, in pH, from 6 to 9, at 0 to 25° C. of reaction temperature for several minutes to 12 hours.

A method of polymer activation consists of the following steps of: preparing the polymer into polyalkylene oxide (hereinafter, referred to as "PAO") such as monomethoxy-poly(ethylene glycol), mPEG); and activating or changing one end of the PAO into a reaction group having reactivity. The activated polymer forms the peptide-polymer conjugate by reacting with e-amine group of lysine. Besides the amine group of lysine, carboxy group, activated carbonyl group, oxidized sugar and mercapto group in the peptide can be used as a conjugated moiety.

The present inventors have measured the blood concentration of peptide according to time after the peptide-polymer conjugate is administered to rats through the nasal cavity. Thus, the present inventors have confirmed that the peptide by the nasal transmucosal delivery has a better stability in living body and sustains its biological activity for a long time.

The peptide of the present invention is not limited to the specific therapeutic agents but applied to the all substances having biological activity. In particular, it is desirable to use calcitonin, parathyroid hormone (hereinafter, referred to as "PTH"), insulin, synthetic enkephalin, growth hormone releasing peptide (hereinafter, referred to as "GHRP"), leutenizing hormone releasing hormone (hereinafter, referred to as "LHRH") and its derivatives, secretory components of hypothalamus, calcitonin gene related peptide (hereinafter, referred to as "CGRP") and thyroid stimulating hormone and thymic humoral factor(hereinafter, referred to as "THF").

Calcitonin is a single chain peptide composed of 32 amino acids, forms a ring at N-terminus and has a proline amide group at C-terminus. Calcitonin inhibits a bone absorption by acting directly to osteoclast and is used for cure of hypercalcemia, Paget's disease, pain from the bone absorption and osteoporosis. Calcitonin is produced in salmon, eel, human, pig, etc., and salmon and eel calcitonin have the most effect.

Parathyroid hormone (PTH) is a peptide hormone composed of 84 amino acids and secreted from parathyroid. Since parathyroid cells have a recognition site for calcium concentration, PTH secretion increases when calcitonin is lower, and PTH secretion decreases when calcitonin higher. PTH increases a calcium absorption taken from foods at the small intestine, transfers calcium from bone to blood, and, finally, increases a blood calcium concentration. The major active site of PTH is adrenal cortex. PTH binds to the membrane of adrenal cortex to increase the production of cAMP, IP3 (inositol triphosphate) and DAG (diacyl glycerol).

Insulin is a peptide composed of A chain and B chain. A chain composed of 21 amino acids and B chain composed of 30 amino acids are connected by 1 pair of disulfide bonds. The disulfide bond exists between 6th amino acid of A chain and 11th amino acid of B chain.

When blood sugar level is increased, insulin is immediately excreted from pancreas. Sugar is, then, stored in the form of glycogen by insulin or used as energy source for fat or protein synthesis. In addition, insulin plays an important role in homeostasis of calcium. When insulin presents at a high concentration, calcium uptake is increased from cell exterior to cell interior and hypercalcemia is induced.

Enkephalin is a pentapeptide representing a similar action to opium. Enkephalin is divided into two groups: methionine enkephalin and leucine enkephalin, according to which C-terminus is bonded to Tyr-Gly-Gly-Phe (SEQ ID NO: 1). Enkephalin inhibits pain transfer to the brain by preventing release of substance P from the ends of analgesic nerve fibers.

Growth hormone releasing peptide (GHRP) presents in the form of hepta and hexa and affects a release of growth hormone. The growth hormone releasing effect of GHRP is related to a dose, increases until adolescence and decreases thereafter.

GHRP-6 is a hexapeptide having a structure of His-Asp-Tyr-Ala-Tyr-Asp-Lys-$NH_2$ (SEQ ID NO: 2), and is very stable in acetate buffer ranged, in pH, from 5.5 to 6.0. In case of oral administration, bioavailability of GHRP-6 is 0.3%, the absorption half life is 15 minutes, and the elimination half life is 60 minutes. GHRP-6 secretes growth hormone selectively through a receptor in hypothalamus and pituitary gland.

Leuteinizing hormone releasing hormone (LH-RH) is a hypothalamus peptide and stimulates the release of LH and follicle stimulating hormone. LH-RH regulates a function of brain and many peripheral organs by binding to receptors on the targeted cell surface. LH-RH has a decapeptide structure of Pyro-Glu-His-Trp-Ser-Tyr-Gly-Leu-Arg-Pro-Gly-$NH_2$ (SEQ ID NO: 3), and is degraded in tubules of the kidney. By way of example, LH-RH derivatives include nafarelin, busecilin, zilidexin, etc.

Pharmaceutical compositions for the nasal transmucosal delivery including the peptide-polymer conjugates of the present invention can be formulated into the suitable form, and mainly administered by spray as a medicine for external use.

For preparation of spray, the peptide-polymer conjugate is dissolved in a solvent, or a suspended, medicinal solution is filled in a container having a specific spraying device (valve) with a low viscous spraying agent. For this, the medicinal solution is sprayed in a type of mist or aerosol smog using pressure. The container may be any suitable material known to those of ordinary skill, including metals such as a tinned iron and aluminum.

If necessary, the inside of container is coated with moth-proof painting. When a internal volume is lower than 100 ml, a container made of glass or synthetic resin is possible. The spraying agents used generally include compressed air and an incombustible liquefied gas such as Freon (Freon 11, $CC_{13}F$; Freon 12, $CC_{12}F$; freon 114, $C_2C_{12}F4$).

The dose of the pharmaceutical compositions containing the peptide-polymer conjugate of the present invention can range from about 0.1 ug to about 10 mg/kg/day, and can be widely altered according to the kind of peptide and patient's condition.

EXAMPLES

Practical and presently preferred embodiments of the present invention are illustrative as shown in the following Examples. However, it will be appreciated that those skilled in the art, on consideration of this disclosure, may make modifications and improvements within the spirit and scope of the present invention.

Example 1

Preparation of PEG-sCT

<1-1> Preparation of PEG5000-sCT

According to the method of Abuchowski (Abuchowski et al, Cancer Biochem. Biophys., 7, 175–86, 1984), monomethoxy-poly(ethylene glycol) was prepared from PEG (MW 5000) so that one hydroxyl group of PEG was protected. Phosgene and N-hydroxysuccinimide was added to it to activate in the form of succinyl-N-hydroxysuccimide ester (hereinafter, referred to as "SS-PEG"). 4.38 mg of the activated SS-PEG was dissolved in phosphate buffer (pH 8.0), added with 0.2 ml of salmon calcitonin (hereinafter, referred to as "sCT") (Novabiochem, LA Jolla, Calif., USA) (5 mg/ml, 0.1 M phosphate buffer, pH 8.0), and stirred for 30 minutes at ambient temperature. 0.1 M glycine was added to stop the reaction. Unreacted calcitonin and PEG were removed by analysis using phosphate buffered saline (hereinafter, referred to as "PBS", pH 7.4) to obtain PEG5000-sCT.

<1-2> Preparation of PEG12000-sCT

PEG (MW 12000) was activated with succinimidyl succinate, and PEG12000-sCT was prepared by using 9.2 mg of the activated SS-PEG. All procedures were performed as indicated in the Example <1-1>.

<1-3> Preparation of PEG2000-sCT

PEG (MW 2000) was activated with succinimidyl succinate, and PEG2000-sCT was prepared by using 2 mg of the activated SS-PEG. All procedures were performed as indicated in the Example <1-1>.

Example 2

Isolation of PEG-sCT

Figure 1:
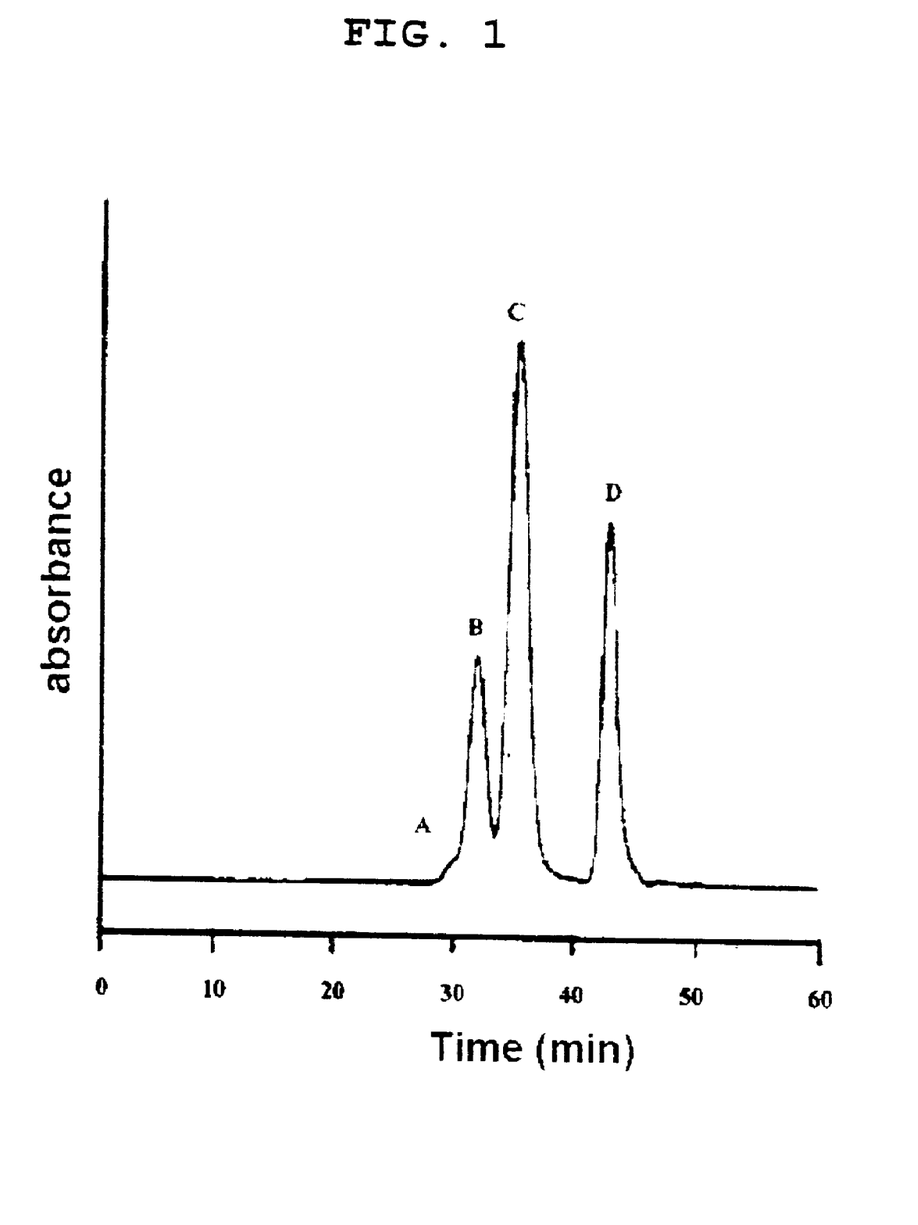
FIG. 1 represents the result of size exclusion chromatography which isolates sCT and PEG-sCT, where A; tri-PEG-sCT, B; di-PEG-sCT, C; mono-PEG-sCT, D; sCT.

PEG-sCT conjugates prepared in the Examples <1-1> to <1-3> were isolated with the aid of size exclusion column (Super HR 12/30, PharmaciaLKB, Sweden) using PBS (pH 7.0) as eluent at 0.4 ml/min of flow rate (FIG. 1).

The peptides isolated from the column as a time difference according to the molecular size was isolated into each peak using fluorescence spectrometer (Hitach, Japan). Each isolated fraction was concentrated using Centricon-10 (Amicon, USA) and stored at refrigerator.

FIG. 1 represented a fluorescence intensity of each peak measured by fluorescence spectrometer wherein each peak was eluted from the size-exclusion column.

As illustrated in the FIG. 1, tri-PEG-sCT which was 1 molecule of calcitonin conjugated with 3 molecules of PEG had the biggest molecular size and was eluted from the column first and collected within 30 minutes after sample injection into the column. After the tri-PEG-sCT, the di-PEG-sCT and mono-PEG-sCT were isolated in succession.

In addition, since calcitonin molecule conjugated with PEG had the smallest molecular size, it was eluted last from the column and time for elution took more 40 minutes. At that time, the fluorescence intensity of each peak eluted from the column had measured by the fluorescence spectrometer directly connected to the column, and each peak was collected.

Example 3

Preparation of PEG-sCT According to Various pHs, Molar Ratios and Reaction Times <3-1> Preparation of PEG-sCT According to pH To 88.2 ul of each of 0.1 M phosphate buffered solutions ranging, in pH, from 5 to 9, 6.8 ul of calcitonin (10 mg/ml) and 5 ul of SS-PEG (60 mg/ml) were added and stirred for 30 minutes at ambient temperature. Addition of 5 ul of 1 M glycine ceased the reaction between calcitonin and SS-PEG. Unreacted calcitonin and PEG were removed by dialysis using PBS (pH 7.4).

<3-2> Preparation of PEG-sCT According to Molar Ratio of SS-PEG/Calcitonin

To 6.8 ul of calcitonin (10 mg/ml), 10 ul of SS-PEG solutions were added to give mixtures of calcitonin and SS-PEG at molar ratios of 1:1, 1:2, 1:3, 1:5 and 1:10 and these five mixtures were added with 78.2 ul of a PBS (pH 8.0). From them, PEG-sCT was prepared in the same procedure as in Example <3-1>.

<3-3> Preparation of PEG-sCT According to Reaction Time 6.8 ul of calcitonin (10 mg/ml) was added with 10 ul of an SS-PEG solution to give a mixture of calcitonin and SS-PEG in a molar ratio of 1:3, and then, five copies of reaction solutions were prepared by adding to the mixture with 78.2 ul of PBS (pH 8.0). Five copies of this solution were allowed to react at room temperature for 5, 10, 20, 30 and 60 min with stirring to prepare PEG-sCT as indicated in Example <3-1>.

Example 4

Isolation of Mono-PEG-Calcitonin Isomer

With the aid of size-exclusion columns, PEG-sCT conjugates prepared in Examples <3-1> to <3-3> were separated into tri-PEG-sCT, di-PEG-sCT and mono-PEG-sCT. This separation was conducted in a similar manner to that of Example 2.

The mono-PEG-sCT obtained was divided into three isomers by reverse phase high performance liquid chromatography (HPLC). In this regard, 100RP-8 (4.0×125 MM, 5 uM, Merck) used as a column while a linear gradient of pentafluoropropionic acid (PFPA)-containing acetonitrile was used as a mobile phase.

The gradient condition was changed with 36–42% solvent B (0.1% PFPA added acetonitrile) and 64–58% solvent A (0.1% PFPA added distilled water).

Quantitative measurements were made using a UV absorption meter (215 mm) or a fluorescent absorption meter (excitation 280 nm, emission 315 nm).

Figure 2:
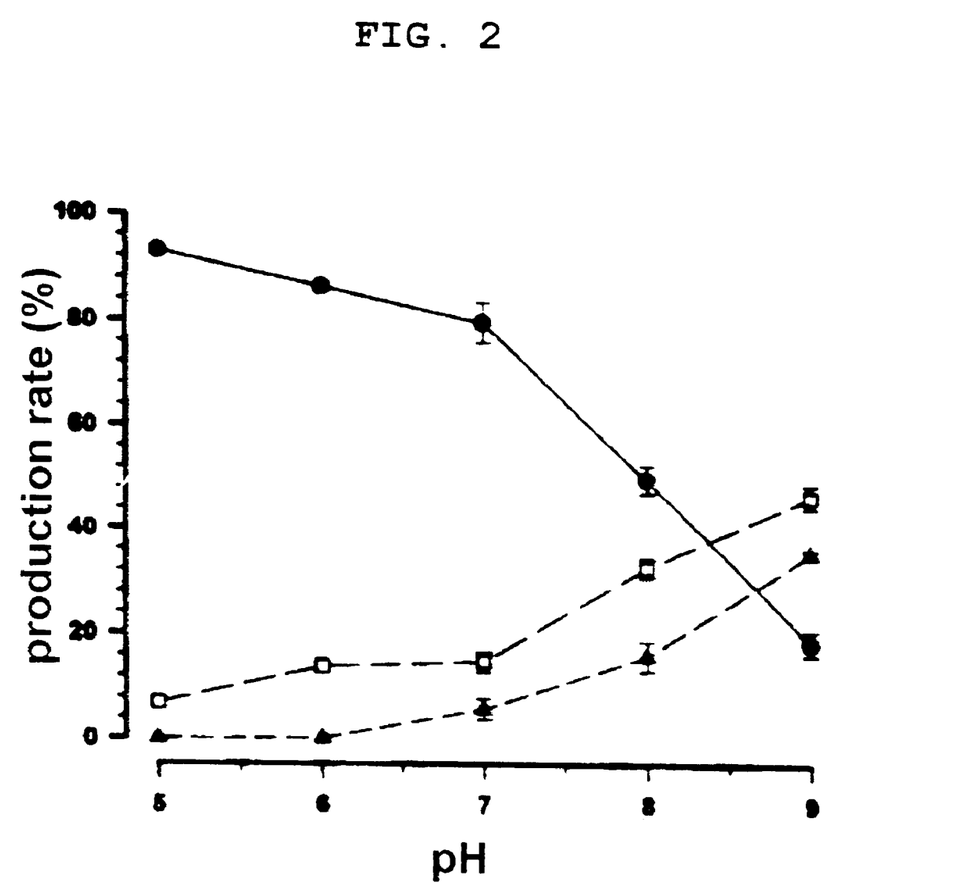
FIG. 2 shows the pH effect on the production of mono-PEG-sCT when PEG is conjugated with N-terminus of calcitonin, $Lys^{18}$ or $Lys^{11}$, where ●; mono-PEG-sCT(N-terminal conjugate), □; mono-PEG-sCT($Lys^{18}$-conjugate), ▲; mono-PEG-sCT($Lys^{11}$1-conjugate).
Figure 3:
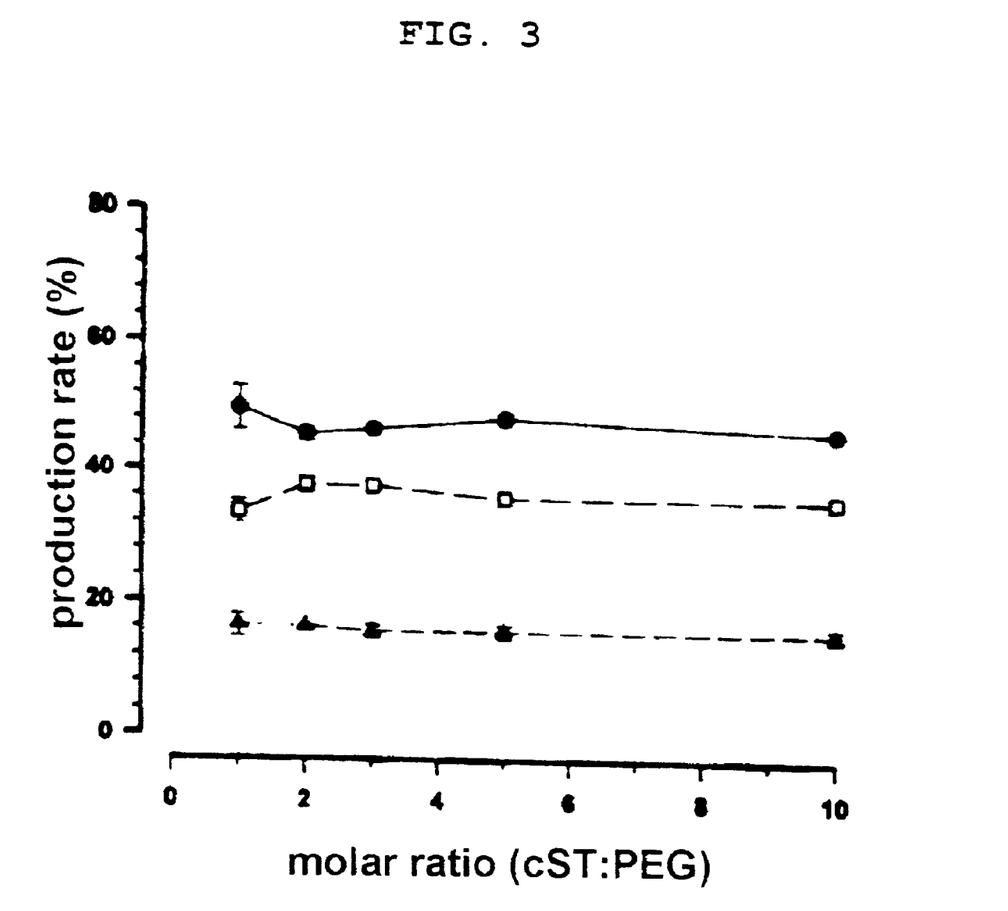
FIG. 3 shows the molar ratio effect of calcitonin:sCT in the production of mono-PEG-sCT when PEG is conjugated with N-terminus of calcitonin, $Lys^{18}$ or $Lys^{11}$, where ●; mono-PEG-sCT(N-terminal conjugate), □; mono-PEG-sCT($Lys^{18}$-conjugate), ▲; mono-PEG-sCT($Lys^{11}$-conjugate).
Figure 4:
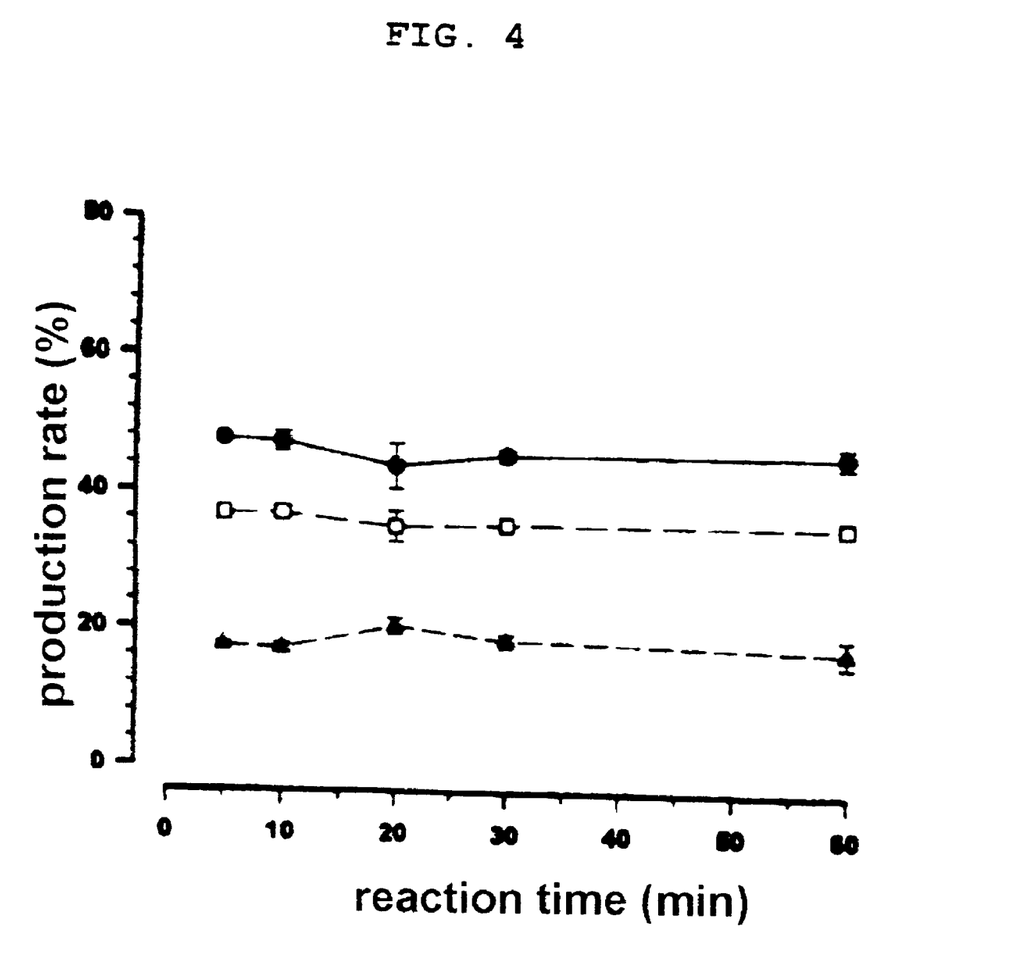
FIG. 4 shows a reaction time effect of calcitonin:sCT in the production of mono-PEG-sCT when PEG is conjugated with N-terminus of calcitonin, $Lys^{18}$ or $Lys^{11}$, where ●; mono-PEG-sCT(N-terminal conjugate), □; mono-PEG-sCT($Lys^{18}$-conjugate), ▲; mono-PEG-sCT($Lys^{11}$-conjugate).

Amino acid analysis showed that the three mono-PEG-sCT isomers thus separated were identified to contain PEG conjugated to the N-terminus, $Lys^{18}$ and $Lys^{11}$ of calcitonin, respectively. In addition, it was found that when the reaction solution was 5, 6 or 7 in pH, more than 80% of PEG was selectively conjugated to the N-terminus. At pH 8 or higher, PEG was increasingly conjugated to the $Lys^{11}$ and the $Lys^{18}$, as shown in FIG. 2. However, there were no differences in the proportion of isomers when the reaction time and the molar ratio were changed, as shown in FIGS. 3 and 4.

Example 5

Preparation and Isolation of PEG-PTH(1-34)

<5-1> Preparation and Isolation of PEG5000-PTH(1-34)

50 ul of SS-PEG5000 (23 mg/0.20 ml, MW 5,000, 0.1 M PBS, pH 7.0) was added with 50 ul of a PTH solution (2.4 mg/0.15 ml, 0.1 M PBS, pH 7.0) to give a mixture containing a molar ratio of 5:1 of SS-PEG5000:PTH. The mixture was allowed to react for 30 min at ambient temperature with shaking. After 30 min of the reaction, an excess amount of a 0.1 M glycine solution was added to stop the reaction. Unreacted parathyroid gland hormone and PEG were removed by dialysis using PBS to obtain PEG5000-PTH(1-34).

Figure 5:
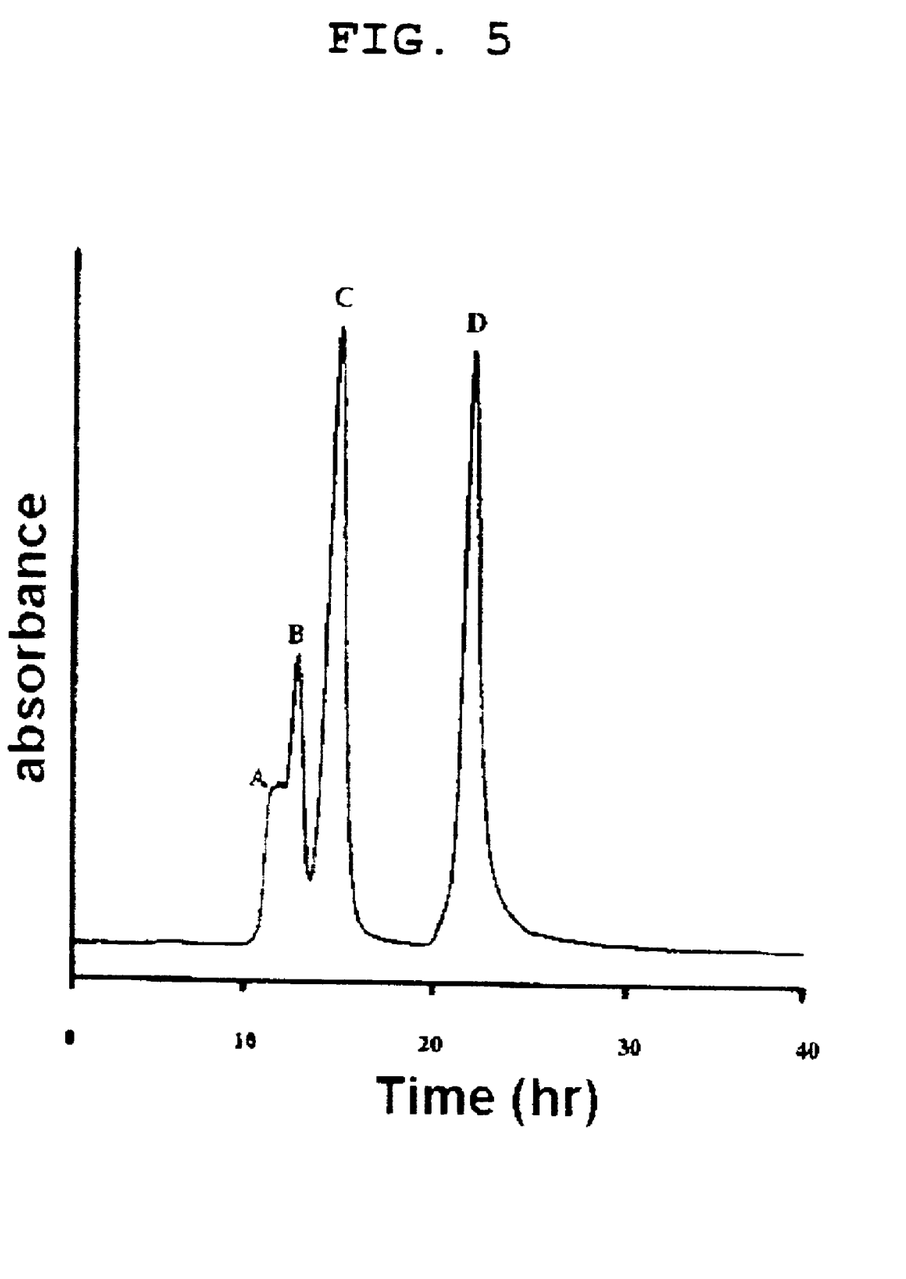
FIG. 5 represents a result of size exclusion chromatography which isolates hPTH and PEG-hPTH(1-34), where A ; tri-PEG-hPTH(1-34), B ; di-PEG-hPTH(1-34), C ; mono-PEG-hPTH(1-34), D ; hPTH(1-34).

The PEG 5000-PTH(1-34) conjugate thus prepared was purified by size-exclusion chromatography using an HPLC system and superdex. For this, PBS (pH 7.0) was used as a developing buffer at a flow rate of 0.8 ml/min. Eluted fractions were stored at 4° C. until they were measured for UV absorbance. UV absorbance was measured at 215 nm while the excitation and emission waves of fluorescence were fixed in the range of 280 to 315 nm, as shown in FIG. 5.

<5-2> Preparation and Isolation of PEG2000-PTH(1-34)

PEG2000-PTH(1-34) conjugates were prepared and isolated in a similar manner to that of Example <5-1> except that SS-PEG2000 was used at an amount of 2 mg.

Example 6

Preparation and Isolation of PEG-GHRP

<6-1> Preparation and Isolation of PEG5000-GHRP-6

50 ul of SS-PEG5000 (23 mg/0.20 ml, MW 5,000, 0.1 M PBS, pH 7.0) was added with 50 ul of a GHRP-6 solution (0.6 mg/0.15 ml, 0.1 M PBS, pH 7.0) to give a mixture containing a molar ratio of 5:1 of SS-PEG: GHRP-6, prepared PEG-GHRP-6, and isolated and purified as indicated in the Example <5-1>. Isolated mono-PEG-GHRP-6 was immediately frozen-dried by freeze dryer.

<6-2> Preparation and Isolation of PEG2000-GHRP-6

Except for use of PEG2000, PEG2000:GHRP-6 conjugate as indicated in the Example <6-1>.

Example 7

Preparation and Isolation of PEG-LHRH

<7-1> Preparation and Isolation of PEG5000-LHRH 50 ul of SS-PEG5000 (23 mg/0.20 ml, MW 5,000, 0.1 M PBS, pH 7.0) was added with 50 ul of a LHRH solution (0.5 mg/0.1 ml, 0.1 M PBS, pH 7.0) to give a mixture containing a molar ratio of 1:5 of LHRH:SS-PEG, prepared PEG-LHRH, and isolated and purified as indicated in the Example <5-1>.

<7-2> Preparation and Isolation of PEG2000-LHRH

Except for use of PEG2000, PEG2000-LHRH conjugate was prepared, isolated and purified as indicated in the Example <7-1>.

Example 8

Preparation and Isolation of PEG5000-triptorelin

Except for use of triptorelin, LHRH derivative, instead of LHRH, PEG5000-triptorelin conjugate was prepared, isolated and purified as indicated in the Example <7-1>.

Example 9

Preparation and Isolation of PEG5000-orntide

Except for use of orntide, LHRH agonist, instead of LHRH, PEG5000-orntide conjugate was prepared, isolated and purified as indicated in the Example <7-1>.

Experimental Example 1

Comparison of Calcium Reduction Effect of sCT and PEG-sCT

SD (Sprague Dawley) male rat (220–300 g, Charles River Japan, Atsugi, Japan) was put under anesthesia by administrating 45 mg/kg of peptobarbital into interperitoneal. Bronchus and esophagus were cannulated with PE-250 tube and thigh arteria with SP-45 tube. 20 ul of a placebo and experimental drugs were administered into the nasal cavity of rats with a Hamilton syringe. The placebo used physiological saline and the experimental drug used PEG5000-sCT, PEG12000-sCT, PEG2000-sCT and sCT prepared from the Example 2. Salmon calcitonin was administered at dose of 0.05 to 4.5 IU per rat, and rats were grouped into 4. 200 ul of blood was taken at before, 5, 10, 30, 60, 120, 240, 480 and 360 minutes after the placebo and the experimental drugs were administered, and immediately centrifuged to obtain 100 ul of plasma. The calcium concentration in plasma was measured using a calcium assay kit (Sigma, USA), and calcium remaining efficiency was calculated as the calcium concentration before administration was 100. The unit of the measured calcium concentration in plasma was mg/dl, and the remaining efficiency was calculated as the ratio (%) to the primary value.

Figure 6:
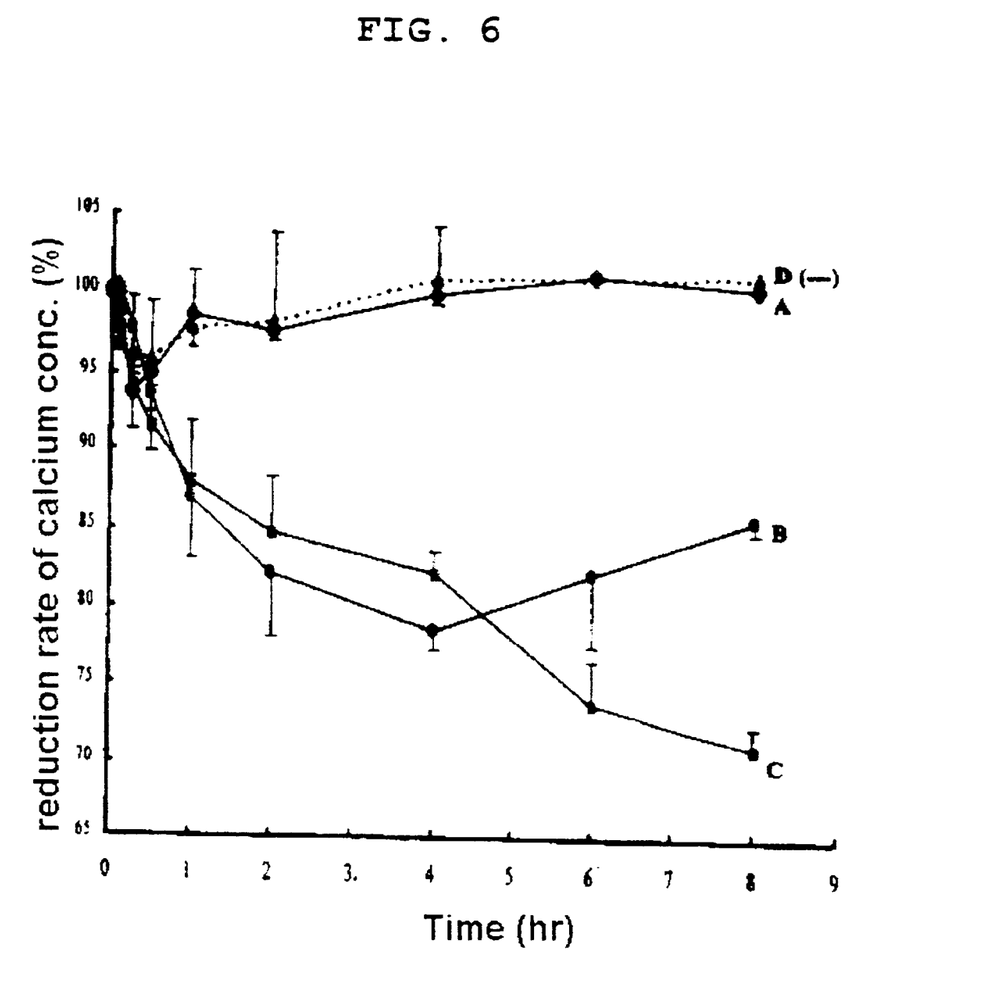
FIG. 6 shows a reduction effect of calcitonin concentration in blood when sCT and PEG-sCT conjugates are administered through the nasal cavity, where A ; sCT, B ; mono-PEG5000-sCTs, C ; mono-PEG2000-sCTs, D ; mono-PEG12000-sCTs.

After the remaining coefficient was calculated according to each time, area-under the curve (AUC) was calculated about the average value of remaining coefficient at each time per experimental group. The reduction ratio of calcium concentration was calculated by the mathematical formula 1, and the results were represented in the table 1 (FIG. 6).

<Mathematical Formula 1>

$$IrD(\%)=[(AUC_{Ca-plac}-AUC_{Ca-sCT})/AUC_{Ca-plac}]100$$

where, $AUC_{Ca-plac}$ was AUC from placebo administration to 960 minutes, and $AUC_{Ca-sCT}$ was AUC from calcitonin and experimental drugs administration to 960 minutes.

TABLE 1

The reduction ratio of calcitonin concentration in plasma at each time (n = 4)

| Time | sCT | PEG5000-sCT | PEG12000-sCT | PEG2000-sCT |
|------|-----|-------------|--------------|-------------|
| 0 | 100% | 100% | 100% | 100% |
| 5 | 98.9% | 199.3% | 96.8% | 97.9% |
| 10 | 93.7% | 97.7% | 96.2% | 94.5% |
| 30 | 95% | 93.6% | 95.0% | 91.5% |
| 60 | 98.7% | 86.9% | 97.0% | 88.0% |
| 120 | 97.8% | 82.2% | 98.4% | 84.8% |
| 240 | 100.3% | 73.9% | 101.3% | 82.2% |
| 480 | 101.6% | 82.3% | — | 73.9% |
| 960 | 101% | 85.8% | 101.8% | 71.2% |

As illustrated in the table 1, the calcium concentration of calcitonin conjugated without any PEG was decreased for 1 hour after the nasal transmucosal administration, but restored at the original concentration after 2 hours. However, when calcitonin conjugated with PEG was administered, the calcitonin reduction effect represented for 4 hours to 8 hours after the nasal transmucosal administration. In addition, the calcium reduction effect was significantly altered according to the molecular size of PEG.

Namely, in case of lower 5,000 of molecular weight, the calcium reduction effect was similar sustained, but, in case of 12,000, the calcium reduction effect was not sufficient. This result was because that the more the molecular weight of PEG was increased, the more the degree of absorption into body through the nasal transmucosal was decreased.

Consequently, calcitonin conjugated with the lower molecular weight of PEG had a better calcitonin reduction effect than calcitonin conjugated without any PEG, and its calcium reduction effect was sustained for a long time.

Therefore, the nasal transmucosal delivery using the PEG conjugates of the present invention could reduce the amount of calcitonin used and side effects of drugs.

Experimental Example 2

Comparison of Calcium Reduction Effect of Mono-PEG-sCT Isomers

Figure 7:
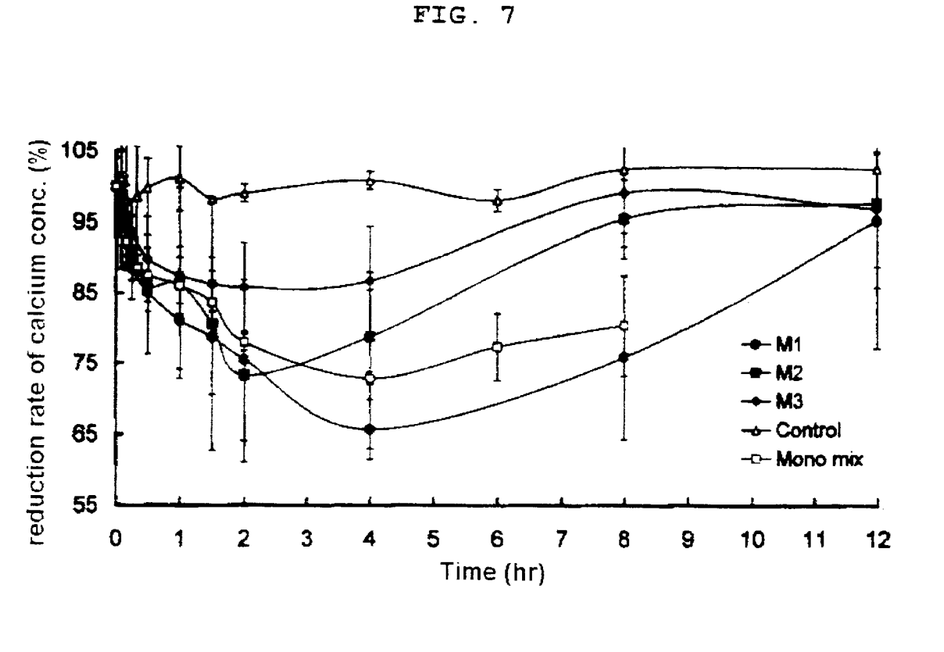
FIG. 7 shows a calcium reduction effect of isolated mono-PEG-sCT isomers, where

The calcium reduction effect of the mono-PEG-sCT isomers prepared from the Example 4 was measured as indicated in the Example 1 (FIG. 7).

As illustrated in the FIG. 7, isomers conjugated with PEG at N-terminus and $Lys^{18}$ represented a better sustaining and effective calcium reduction effect than isomers conjugated with PEG at $Lys^{11}$. In addition, in case of mono-PEG-sCT not isolated, $Lys^{18}$ isomers having a lower calcium reduction effect than N-terminus isomers represented a considerable reduction effect to sCT or $Lys^{11}$ isomers.

Example 10

Preparation and Isolation of PEG2000-GLP-1 (Glucaaons Like Peptide)

PEG (MW 2000) was activated with succinimidyl succinate, and PEG2000-GLP-1 was prepared by using 2 mg of the activated SS-PEG. All procedures were performed as indicated in the Example <1—1>. In addition, PEG2000-GLP-1 was isolated and purified as indicated in the Example <5-1>.

INDUSTRIAL APPLICABILITY

A pharmaceutical composition comprising a peptide-polymer conjugate for a nasal transmucosal delivery of the present invention increases the water solubility of peptides, which are sparingly soluble in water, improves their stability by protecting from being degraded by proteases, and, consequently, reduces the number administrations of drug to decrease side-effects induced by drug abuse.

In addition, since the pharmaceutical composition comprising a peptide-polymer conjugate for the nasal transmucosal delivery of the present invention is delivered through the nasal cavity, it allows drug activity to be expressed in a short period of time and improves a bioavailability.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A method of treatment, comprising administering an effective amount of a pharmaceutical composition containing calcitonin conjugated to polyethylene glycol via nasal transmucosal delivery to a mammal in need thereof.

2. The method of claim 1, wherein the calcitonin is conjugated to said polyethylene glycol through a member of the group consisting of the N-terminus, the $Lys^{18}$ and the $Lys^{11}$ of said calcitonin.

3. The method of claim 1, wherein the calcitonin is covalently bonded to said polyethylene glycol through the N-terminus of said calcitonin.

4. The method of claim 1, wherein the calcitonin is covalently bonded to said polyethylene glycol through the $Lys^{18}$ of said calcitonin.

5. The method of claim 1, wherein said polyethylene glycol has a molecular weight of from about 200 to about 20,000.

6. The method claim 1, we said polythylene glycol has a molecular weight of from about 500 to about 12,000.

7. The method of claim 1, wherein the molar ratio of said calcitonin to said polyethylene glycol is from about 1:1 to about 1:7.

8. The method of claim 1, wherein from about 1 to about 3 molecules of said polyethylene glycol is conjugated to each calcitonin.

* * * * *